United States Patent
Hong et al.

(10) Patent No.: US 6,805,705 B2
(45) Date of Patent: *Oct. 19, 2004

(54) HYBRID STENT

(75) Inventors: James Hong, San Jose, CA (US); Timothy A. Limon, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/404,419

(22) Filed: Mar. 31, 2003

(65) Prior Publication Data

US 2003/0191524 A1 Oct. 9, 2003

Related U.S. Application Data

(63) Continuation of application No. 09/753,232, filed on Dec. 28, 2000, now Pat. No. 6,565,599.

(51) Int. Cl.[7] .................................................. A61F 2/06
(52) U.S. Cl. ...................................... 623/1.15; 623/1.16
(58) Field of Search .............................. 623/1.13, 1.14, 623/1.15, 1.16, 1.35

(56) References Cited

U.S. PATENT DOCUMENTS

| | | | |
|---|---|---|---|
| 3,868,956 A | 3/1975 | Alfidi et al. | |
| 4,512,338 A | 4/1985 | Balko et al. | |
| 4,553,545 A | 11/1985 | Maass et al. | |
| 4,733,665 A | 3/1988 | Palmaz | |
| 4,762,128 A | 8/1988 | Rosenbluth | |
| 4,800,882 A | 1/1989 | Gianturco | |
| 4,856,516 A | 8/1989 | Hillstead | |
| 4,886,062 A | 12/1989 | Wiktor | |
| 5,383,892 A | * 1/1995 | Cardon et al. | 623/1.16 |
| 5,421,955 A | 6/1995 | Lau et al. | |
| 5,591,224 A | 1/1997 | Schwartz et al. | |
| 5,653,727 A | 8/1997 | Wiktor | |
| 5,843,164 A | * 12/1998 | Frantzen et al. | 623/1.16 |
| 6,066,167 A | 5/2000 | Lau et al. | |
| 6,143,022 A | 11/2000 | Shull et al. | |
| 6,264,687 B1 | * 7/2001 | Tomonto | 623/1.16 |
| 6,283,991 B1 | * 9/2001 | Cox et al. | 623/1.13 |
| 6,315,788 B1 | 11/2001 | Roby | |
| 6,338,740 B1 | 1/2002 | Carpentier | |
| 6,565,599 B1 | * 5/2003 | Hong et al. | 623/1.15 |

FOREIGN PATENT DOCUMENTS

| | | |
|---|---|---|
| DE | 197 28 337 A1 | 1/1999 |
| WO | WO 98/20810 | 5/1998 |

OTHER PUBLICATIONS

International Application Published Under the Patent Cooperation Treaty (PCT) as Publication No. WO 01/01888 A1 to Applicant SciMed Life Systems, Inc., published Jan. 11, 2001.

* cited by examiner

Primary Examiner—Corrine McDermott
Assistant Examiner—Hieu Phan
(74) Attorney, Agent, or Firm—Fulwider Patton Lee & Utecht, LLP

(57) ABSTRACT

The invention is directed to an expandable stent for implantation in a body lumen, such as a coronary artery. The stent consists of radially expandable cylindrical rings generally aligned on a common axis and interconnected by one or more links. At least some of the links are formed of a polymer material providing longitudinal and flexural flexibility to the stent while maintaining sufficient column strength to space the rings along the longitudinal axis.

2 Claims, 8 Drawing Sheets

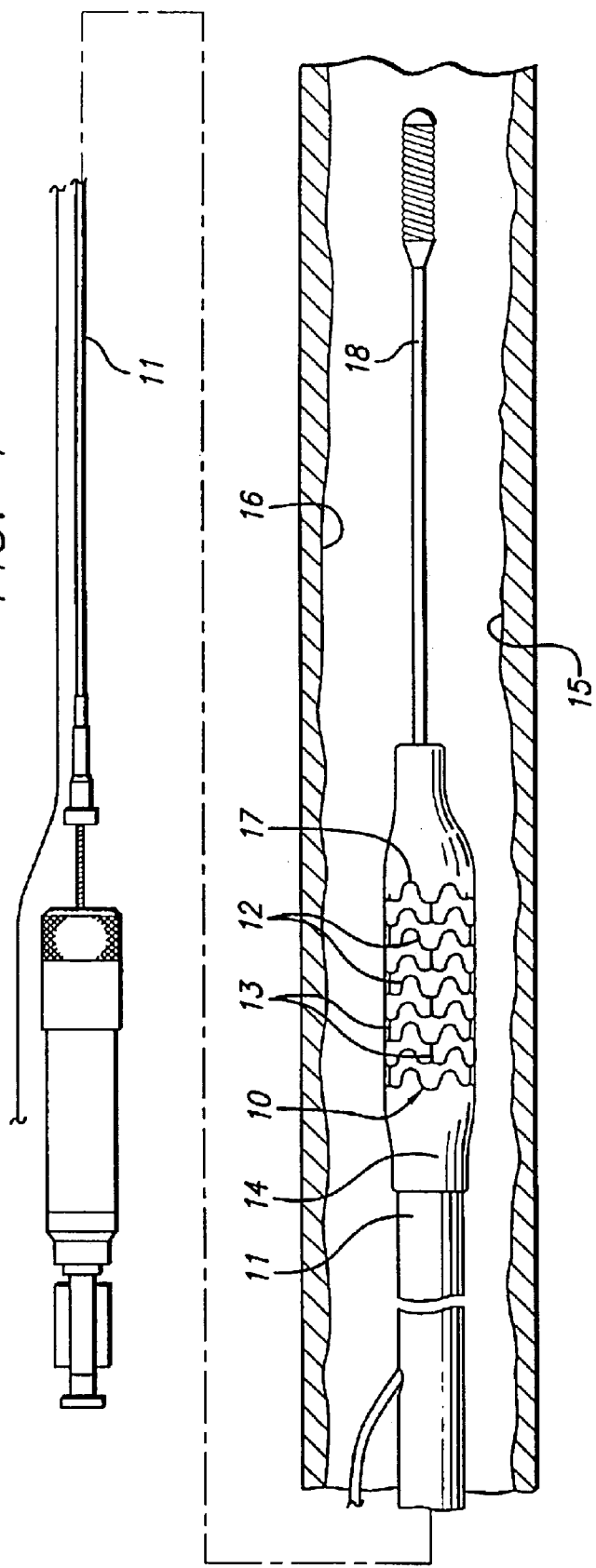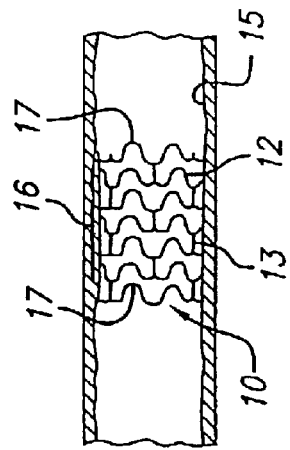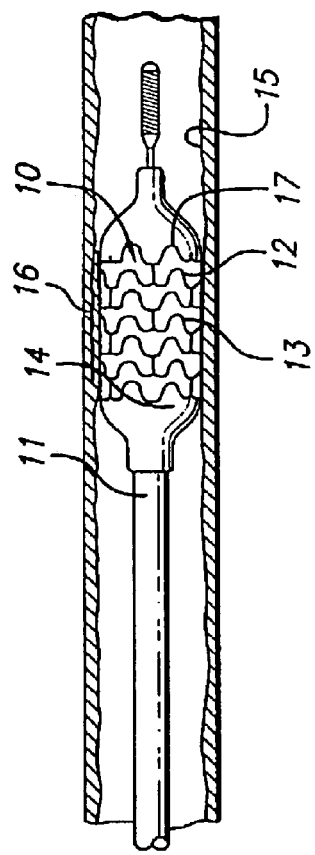

HYBRID STENT

CROSS REFERENCE TO RELATED APPLICATIONS

This is a continuation application of parent application having U.S. Ser. No. 09/753,232 filed Dec. 28, 2000, now U.S. Pat. No. 6,565,599 the contents of which is hereby incorporated by reference.

BACKGROUND OF THE INVENTION

This invention relates to expandable endoprosthesis devices, generally called stents, which are adapted to be implanted into a patient's body lumen, such as blood vessel, to maintain the patency thereof. These devices are useful in the treatment of atherosclerotic stenosis in blood vessels.

Stents are generally tubular-shaped devices which function to hold open a segment of a blood vessel, coronary artery, or other anatomical lumen. They are particularly suitable for use to support and hold back a dissected arterial lining which can occlude the fluid passageway therethrough.

Further details of prior art stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 6,066,167 (Lau et al.); and U.S. Pat. No. B1 5,421,955 (Lau et al.), which are incorporated herein in their entirety by reference thereto.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery. Once the stent is mounted on the balloon portion of the catheter, it is often delivered through tortuous vessels, including tortuous coronary arteries. The stent must have numerous properties and characteristics, including a high degree of flexibility in order to appropriately navigate the tortuous coronary arteries. This flexibility must be balanced against other features including radial strength once the stent has been expanded and implanted in the artery. While other numerous prior art stents have had sufficient radial strength to hold open and maintain the patency of a coronary artery, they have lacked the flexibility required to easily navigate tortuous vessels without damaging the vessels during delivery.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. Other types of prior art stents may be formed from a polymer, again all of the component parts being formed from the same polymer material. These types of stents, the ones formed from a metal and the ones formed from a polymer, each have advantages and disadvantages. One of the advantages of the metallic stents is their high radial strength once expanded and implanted in the vessel. A disadvantage may be that the metallic stent lacks flexibility which is important during the delivery of the stent to the target site. With respect to polymer stents, they may have a tendency to be quite flexible and are advantageous for use during delivery through tortuous vessels, however, such polymer stents may lack the radial strength necessary to adequately support the lumen once implanted.

What has been needed and heretofore unavailable is a stent which has a high degree of flexibility so that it can be advanced through tortuous passageways and can be readily expanded and yet have the mechanical strength to hold open the body lumen into which it expanded. The present invention satisfied this need.

SUMMARY OF THE INVENTION

The present invention is directed to an expandable stent which is relatively flexible along its longitudinal axis to facilitate delivery through tortuous body lumens, but which is stiff and stable enough radially in an expanded condition to maintain the patency of a body lumen such as an artery when implanted therein.

The stent of the invention generally includes a plurality of radially expandable cylindrical rings which are relatively independent in their ability to expand and to flex relative to one another. The individual radially expandable cylindrical rings of the stent are formed from a metallic material and are aligned on a common longitudinal axis. The resulting stent structure is a series of radially expandable cylindrical rings which are spaced longitudinally close enough so that small dissections in the wall of a body lumen may be pressed back into position against the lumenal wall, but not so close as to compromise the longitudinal flexibility of the stent. The cylindrical rings are attached to each other by flexible links such that at least one flexible link attaches adjacent cylindrical rings. If desired, more than one link can be used to attach adjacent cylindrical rings. At least some of the links are formed from a polymeric material that provides flexibility to the link and allows the stent to more easily bend or flex along its longitudinal axis as the stent navigates through tortuous vessels or coronary arteries. The flexibility of the links is balanced against the links having sufficient column strength to properly orient and separate the cylindrical rings along the stent longitudinal axis so that the rings do not telescope into each other or overlap one another. The combination of the flexible cylindrical rings and flexible links cumulatively provides a stent which is flexible along its length and about its longitudinal axis, yet is still relatively stiff in the radial direction after it has been expanded in order to maintain the patency of a vessel and to resist collapse.

One preferred structure for the expandable cylindrical rings which form the stent of the present invention is generally a circumferential undulating pattern, e.g., serpentine. The open reticulated structure of the stent allows for the perfusion of blood over a large portion of the arterial wall which can improve the healing and repair of a damaged arterial lining.

The stent embodying features of the invention can be readily delivered to the desired body lumen, such as a coronary artery (peripheral vessels, bile ducts, etc.), by mounting the stent on an expandable member of a delivery catheter, for example a balloon, and advancing the catheter and stent assembly through the body lumen to the target site. Generally, the stent is compressed or crimped onto the balloon portion of the catheter so that the stent does not move longitudinally relative to the balloon portion of the catheter during delivery through the arteries, and during expansion of the stent at the target site.

When the stent expanded, the radial expansion of the expandable cylindrical rings deforms the undulating or serpentine pattern similar to changes in a waveform which result from decreasing the waveform's amplitude and the frequency. The undulating patterns of the individual cylindrical rings can be in phase with each other or out of phase, depending on the stent design. The cylindrical rings of the stent are plastically deformed when expanded so that the stent will remain in the expanded condition and therefore they must be sufficiently rigid when expanded to prevent the collapse thereof in use. During expansion of the stent, portions of the undulating pattern may tip outwardly resulting in projecting members on the outer surface of the expanded stent. These projecting members tip radially outwardly from the outer surface of the stent and embed into the vessel wall and help secure the expanded stent so that it does not move once it is implanted.

The links which interconnect adjacent cylindrical rings may have a transverse cross-section similar to the transverse dimensions of the undulating components of the expandable cylindrical rings. In one embodiment, all of the links are joined at either the peaks or the valleys of the undulating structure of the cylindrical rings. In this manner there is little or no shortening of the stent upon expansion.

The number and location of links connecting the rings can be varied in order to vary the desired longitudinal and flexural flexibility in the stent structure both in the unexpanded as well as the expanded condition. These properties are important to minimize alteration of the natural physiology of the body lumen into which the stent is implanted and to maintain the compliance of the body lumen which is internally supported by the stent. Generally, the greater the longitudinal and flexural flexibility of the stent, the easier and the more safely it can be delivered to the target site.

Other features and advantages of the present invention will become more apparent from the following detailed description of the invention when taken in conjunction with the accompanying exemplary drawings.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery.

FIG. 3 is an elevational view, partially in section, depicting the expanded stent within the artery after withdrawal of the delivery catheter.

DETAILED DESCRIPTION OF THE PREFERRED EMBODIMENTS

Figure 4:
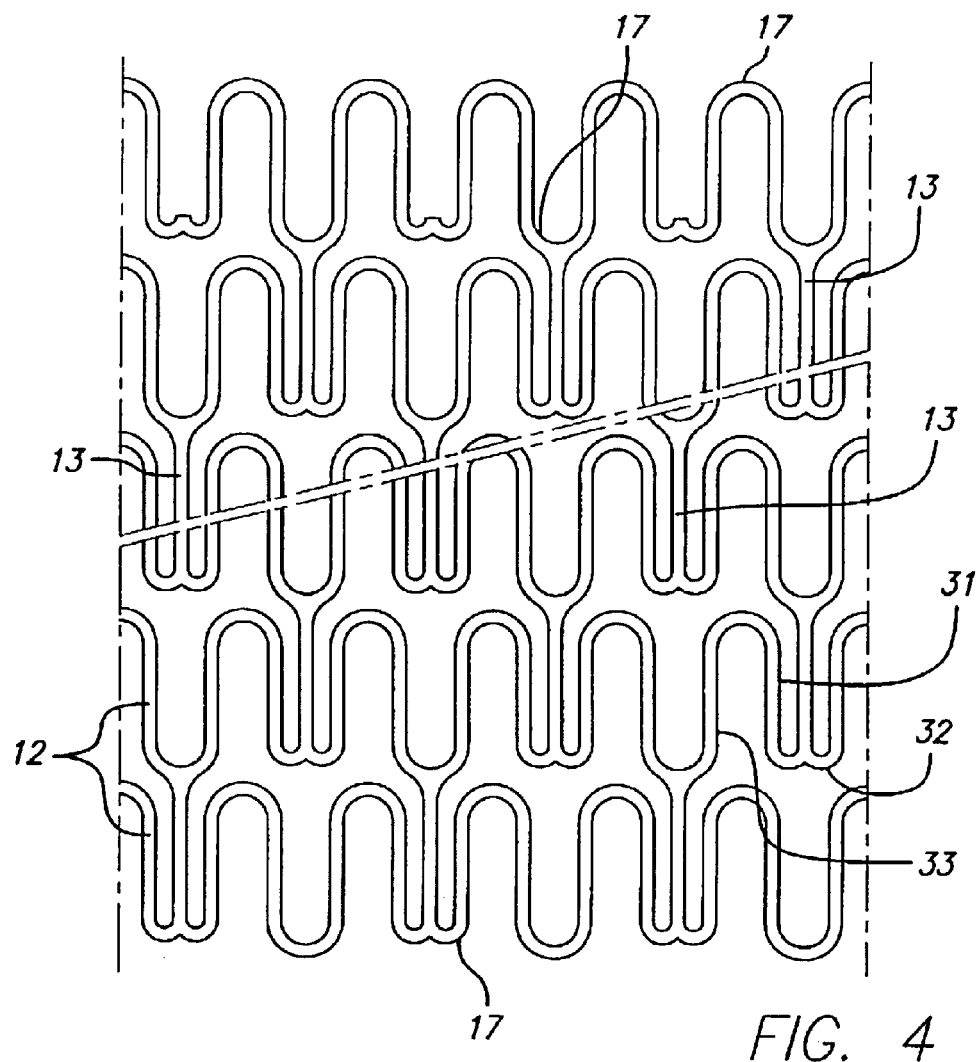
FIG. 4 is a plan view of a flattened section of the stent of the invention, illustrating the cylindrical rings attached by the links.

FIG. 1 illustrates a stent 10 incorporating features of the invention which is mounted onto a delivery-catheter 11. The stent generally comprises a plurality of radially expandable cylindrical rings 12 disposed generally coaxially and interconnected by links 13 disposed between adjacent cylindrical elements. The delivery catheter 11 has an expandable portion or balloon 14 for expanding of the stent 10 within an artery 15. The artery 15, as shown in FIG. 1 has an occluded portion of the arterial passageway that has been opened by a previous procedure, such as angioplasty.

The delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is crimped or compressed onto the balloon in a known manner.

Each radially expandable cylindrical ring 12 of the stent 10 may be substantially independently expanded to some degree relative to adjacent rings. Therefore, the balloon 14 may be provided with an inflated shape other than cylindrical, e.g., tapered, to facilitate implantation of the stent in a variety of body lumen shapes.

In one embodiment, the delivery of the stent 10 is accomplished in the following manner. The stent is first mounted onto the inflatable balloon 14 on the distal extremity of the delivery catheter by crimping or compressing the stent in a known manner. The catheter-stent assembly is introduced within the patient's vasculature in a conventional Seldinger technique through a guiding catheter (not shown). A guide wire 18 is disposed across the damaged arterial section and then the catheter-stent assembly is advanced over a guide wire 18 within the artery 15 until the stent is positioned at the target site 16. The balloon of the catheter is expanded, expanding the stent against the artery, which is illustrated in FIG. 2. While not shown in the drawing, the artery is preferably expanded slightly by the expansion of the stent to seat or otherwise fix the stent to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent from an elongated tubular member or a flat sheet, the undulating component of the cylindrical rings 12 of the stent is relatively flat in transverse cross-section, so that when the stent is expanded, the cylindrical rings are pressed into the wall of the artery and as a result do not interfere with the blood flow through the artery. The cylindrical elements 12 of stent which are pressed into the wall of the artery will eventually be covered with endothelial cell growth which further minimizes blood flow interference. The undulating portion 17 of the cylindrical rings provide good tacking characteristics to prevent stent movement within the artery. Furthermore, the closely spaced cylindrical rings at regular intervals provide uniform support for the wall of the artery 15, and consequently are well adapted to tack up and hold in place small flaps or dissections in the wall of the artery 15.

FIG. 4 is an enlarged plan view of the stent 10 shown in FIG. 1 with one end of the stent shown in an exploded view to illustrate in greater detail the placement of links 13 between adjacent radially expandable cylindrical rings 12. Each of the links on one side of a cylindrical ring is preferably placed to achieve maximum flexibility for a stent. In the embodiment shown in FIG. 4, the stent 10 has three links 13 between adjacent radially expandable cylindrical elements 12, which are spaced 120° apart. Each of the links on one side of a cylindrical ring are offset radially 60° from a corresponding link on the other side of the ring. The alternating link pattern results in a stent having longitudinal and flexural flexibility in essentially all directions due to the placement of the links. Various configurations for the placement of the links are possible, and several examples are illustrated schematically in FIGS. 4–5. However, as previously mentioned, all of the links of an individual stent should be secured to either the peaks or valleys of the undulating structural portions 17 in order to help prevent shortening of the stent during the expansion thereof.

FIG. 4 illustrates a stent of the present invention wherein three links 13 are disposed between radially expandable cylindrical rings 12. The links are distributed radially around the circumference of the stent at a 120° spacing. Disposing four or more links between adjacent cylindrical rings will generally give rise to the same considerations discussed above for placement of one, two, and three links.

Figure 5:
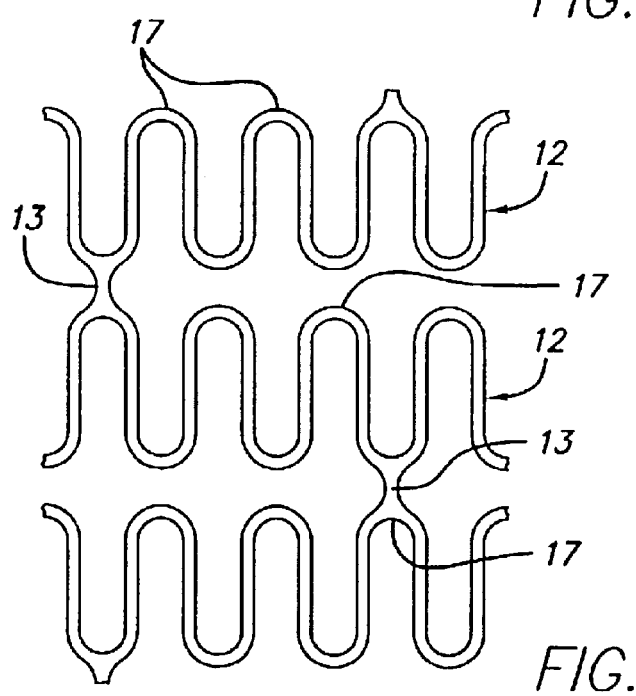
FIG. 5 is a plan view of a flattened section of a stent illustrating an undulating pattern in the expandable cylindrical rings of the stent which are out of phase.

The properties of the stent 10 may also be varied by alteration of the undulating portions 17 of the cylindrical rings 12. FIG. 5 illustrates an alternative stent structure in which the cylindrical rings have an undulating shape so the undulations of one cylindrical ring 12 is out of phase with adjacent cylindrical rings. The particular pattern and how many undulations per unit of length around the circumference of the cylindrical rings, or the amplitude of the undulations, are chosen to fill particular mechanical requirements for the stent, such as radial stiffness.

Figure 6:
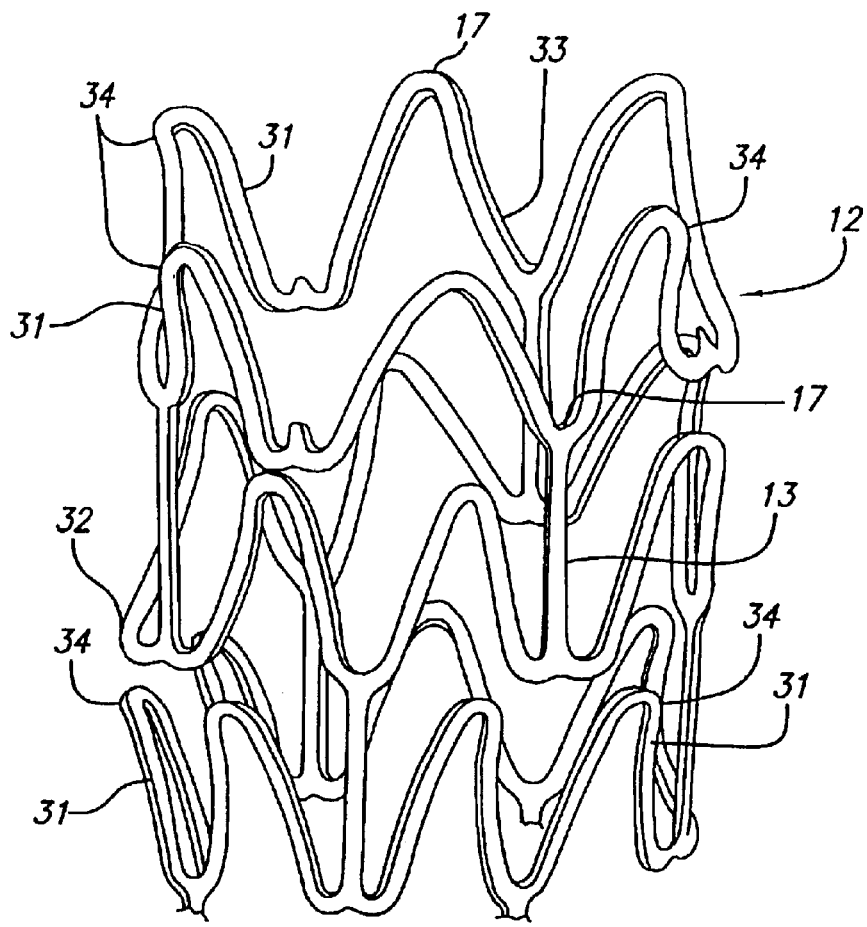
FIG. 6 is a perspective view of the stent of FIG. 4 after it is fully expanded depicting some portions of the stent projecting radially outwardly.

With reference to FIG. 6, the cylindrical rings 12 are in the form of undulation portions 17, as previously mentioned. The undulating portion is made up of a plurality of U-shaped members 31, W-shaped members 32, and Y-shaped members 33, each having a radius that more evenly distributes expansion forces over the various members. After the cylindrical rings 12 have been radially expanded, outwardly projecting edges 34 are formed. That is, during radial expansion some of the U-shaped, W-shaped, or Y-shaped portions may tip radially outwardly thereby forming outwardly projecting edges. These outwardly projecting edges provide for a roughened outer wall surface of the stent 10 and assist in implanting the stent in the vascular wall by embedding into the vascular wall. In other words, outwardly projecting edges embed into the vascular wall, for example artery 15, as depicted in FIG. 3. Depending upon the dimensions of stent 10 and the thickness of the various members making up the serpentine pattern 30, any of the U-shaped members 31, W-shaped members 32, and Y-shaped members 33 can tip radially outwardly to form a projecting edge 34.

The stent patterns shown in FIGS. 1–6 are for illustration purposes only and can vary in shape and size to accommodate different vessels or body lumens. Thus, rings connected by links can have any structural shapes and are not limited to the aforedescribed undulating rings, U-shaped, W-shaped, and Y-shaped portions, or to straight links connecting the rings.

In keeping with the invention, the links 13 are formed from a flexible polymer material, or similar material, that is bendable and flexible to enhance longitudinal and flexural flexibility of the stent 10. Since the cylindrical rings 12 are independently formed out of a metal, such as stainless steel or the like, the rings must be connected together by the links. One aspect of the invention provides for various attachment mechanisms for attaching the links to the rings.

Figure 7:
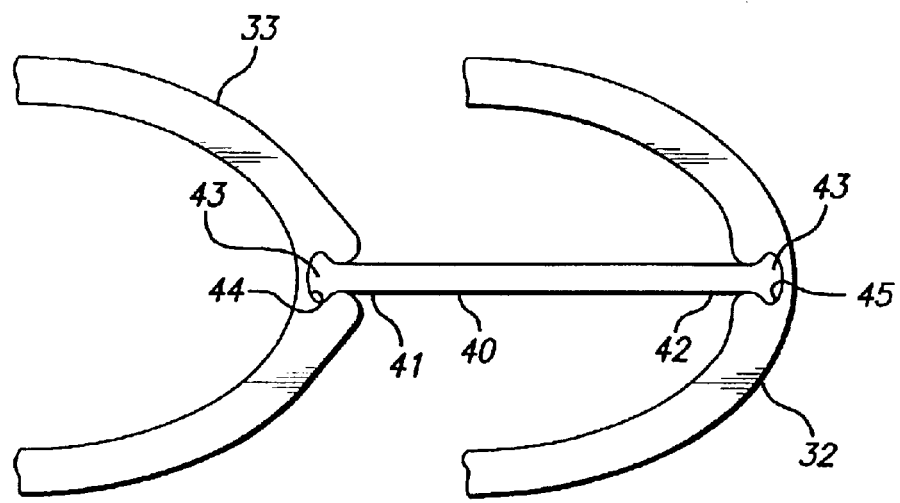
FIG. 7 is a plan view of a flattened section of a portion of two adjacent rings attached by one of the links.
Figure 8:
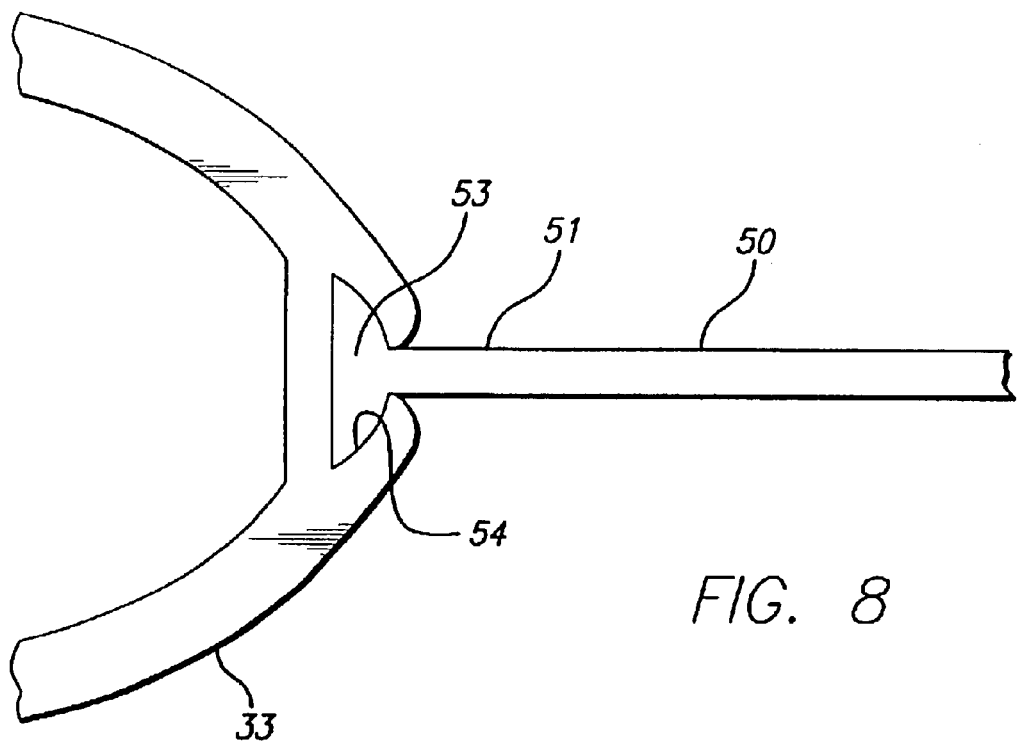
FIG. 8 is a plan view of a flattened section of one cylindrical ring of the stent and a link attached thereto.

As shown in FIG. 7, link 40 has a length which can vary, and connects a Y portion 33 of one cylindrical ring (not shown) to the W-shaped portion 32 of an adjacent cylindrical ring (not shown). The link has a first end 41 and a second end 42 and a locking head 43 which is designed to fit within correspondingly shaped first cavity 44 and second cavity 45 as illustrated in FIG. 7. As will be further described herein, the polymer used to form the links is injection molded so that the locking heads can take any particular form in order to fill the first and second cavities. An alternative link is shown in FIG. 8, where link 50 has a first end 51 that is attached to Y portion 33. In this figure, the other end of the link and the part that it is attached to has been omitted. The link has a locking head 53 that has a different shape than the locking head 43 shown in FIG. 7. Locking head 53 corresponds to the shape of first cavity 54 that has been machined into the apex of Y-shaped member 33. Other shapes for locking heads and corresponding cavities are envisioned, and those shown in FIGS. 7 and 8 are for illustration purposes to show the interlocking relationship between the links and the cylindrical rings.

Figure 9:
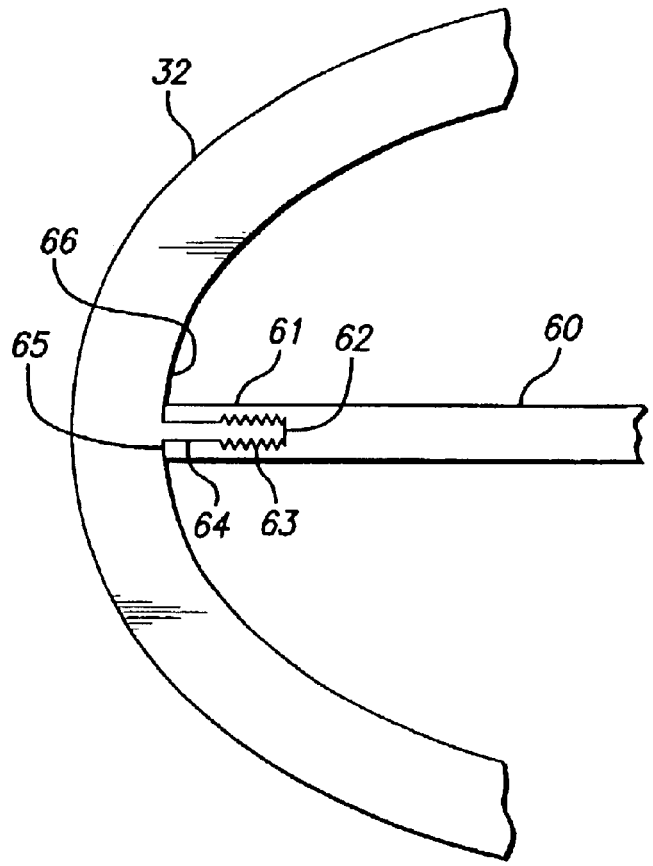
FIG. 9 is a plan view of a flattened section of one cylindrical ring with a link attached thereto.

In another embodiment, as shown in FIG. 9, link 60 has a first end that abuts W-shaped portion 32 which again is part of a cylindrical ring (not shown). In this embodiment, locking head 62 has a plurality of teeth 63 and a smooth portion shaft 64 that are formed as a part of the W-shaped portion 32. The polymer link either is injection molded to surround or encapsulate the locking head or the portion surrounding the locking head can be heated and the polymer link pushed over the teeth and shaft portion of the locking head as the polymer softens from the heated locking head 62. As the structure cools, the polymer link 60 becomes securely fastened to the locking head. In this embodiment, the link tip 65 abuts the curved portion 66 of the W-shaped portion 32. The link 60 can be used to attach any of the U-shaped, W-shaped, or Y-shaped portions 31,32,33.

Figure 10:
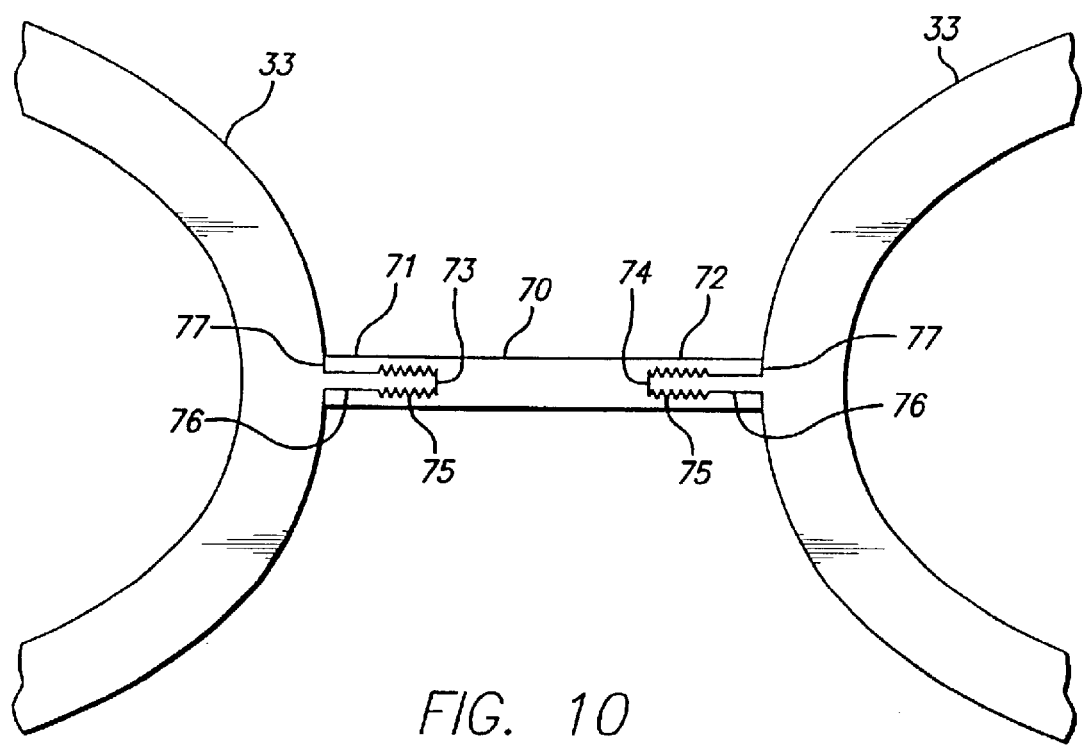
FIG. 10 is a plan view of a flattened section of a portion of two cylindrical rings with a link attached thereto.

In another embodiment shown in FIG. 10, two Y-shaped portions 33 are connected by link 70. The link has a first end 71 and a second end 72 which abuts the peaks of the Y-shaped portions. First end 71 is attached to first locking head 73 and second end 72 is attached to second locking head 74. Each of the locking heads have teeth 75 for gripping the polymer link and a shaft 76 attached to the respective Y-shaped portions 33. Link tip 77 is intended to abut Y-shaped portion 33. As described for the embodiment of FIG. 9, the polymer link 70 can be injection molded as will be further described herein or the locking heads may be heated and the polymer link pushed onto the locking heads and subsequently cooled to form the attachment.

Figure 11:
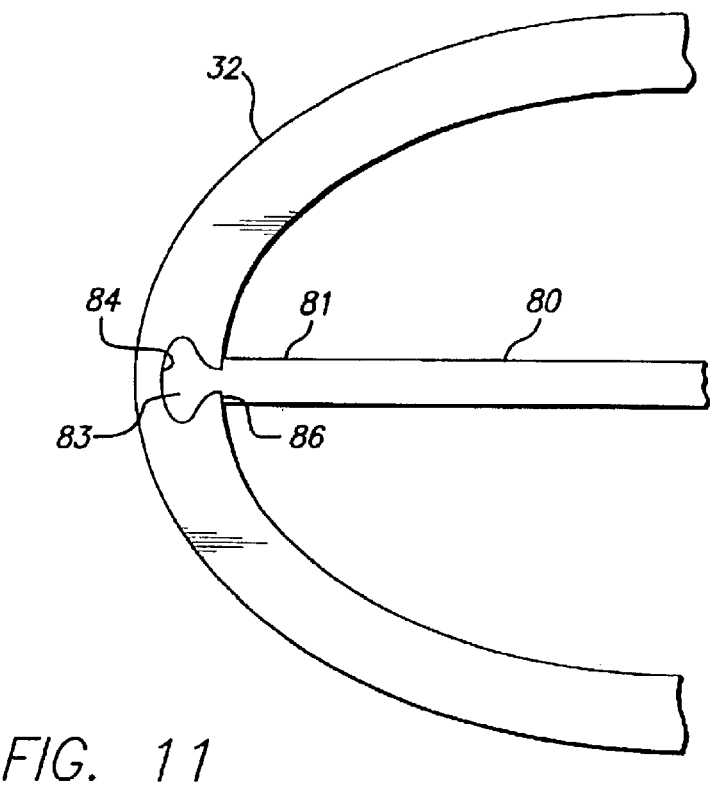
FIG. 11 is a plan view of a flattened section of a portion of one cylindrical ring with a link attached thereto.

In another embodiment shown in FIG. 11, link 80 is attached to and abuts a portion of W-shaped portion 32 of a cylindrical ring (again not shown). In this embodiment, the link has a first end 81 and a locking head 83 that conforms to the shape of first cavity 84 that is formed in W-shaped portion 32. This embodiment differs slightly from that shown in, for example, FIG. 7, in that in this embodiment the link 80 has a link tip 86 that abuts the inner curve surface of the W-shaped portion. As previously described, injection molding the polymer link 80 is one method of forming the attachment and the locking head 83 to attach adjacent cylindrical rings.

Figure 12:
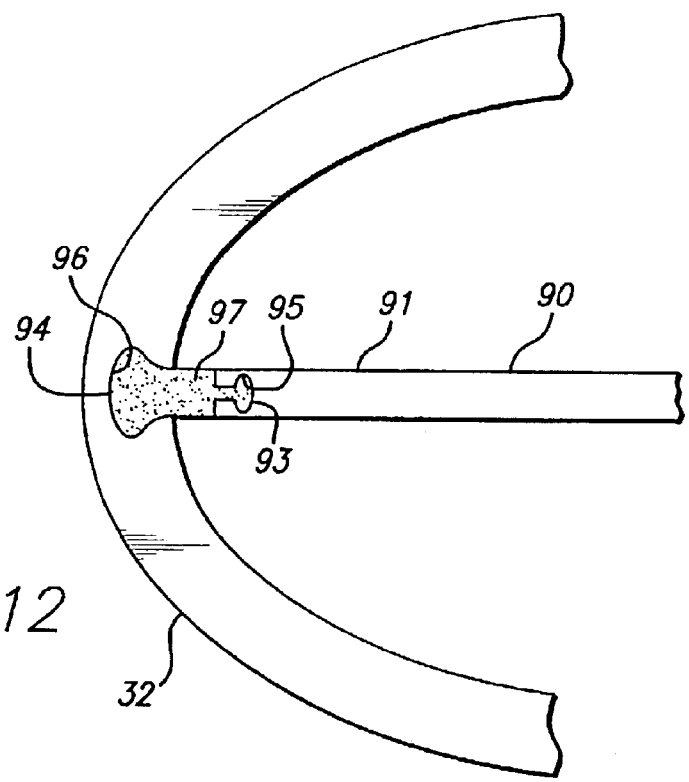
FIG. 12 is a plan view of a flattened section of a portion of a cylindrical ring with a link adhesively bonded thereto.

In another embodiment of the invention, as shown in FIG. 12, the polymer link is attached to a W portion 32 of a cylindrical ring by use of an adhesive. More particularly, link 90 has a first end 91 that is adhesively bonded to the W-shaped portion. A first locking head 93 is associated with the link and a second locking head 94 is associated with the W-shaped portion. The first locking head corresponds to a first cavity 95 formed in the link 90, while the second locking head 94 corresponds to a second cavity 96 formed in the W-shaped portion. The adhesive 97 can be any biocompatible adhesive that is well known, such as a cyanoacrylite-based adhesive. Several adhesives can be used including Locitite 401, 1-06FL, and M-11FL, the latter two of which are urethane-based adhesives. Other adhesives can be used without departing from the spirit and scope of the invention. As can be seen in FIG. 12, the adhesive 97 forms the bond for attaching the link 90 to the W-shaped portion 32. Other shapes for the first locking head and the second locking head 93,94 can be used in order to enhance the attachment force between the link and the W-shaped portion. Alternatively, link 90 can be attached to the metal ring by a lap joint (with the polymer link overlying the connection site) or a butt joint (with the end of the polymer link adhered to the edge of the metal ring).

Figure 13:
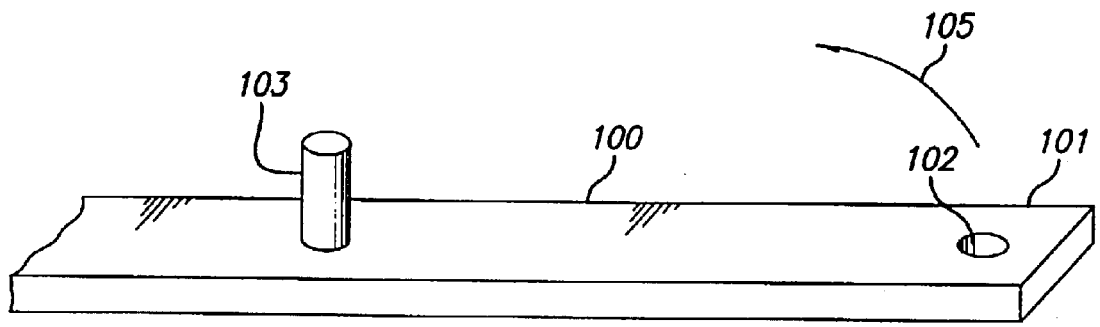
FIG. 13 is an elevational view of a portion of a link depicting an alternative attachment method to attach one cylindrical ring to an adjacent cylindrical ring.
Figure 14:
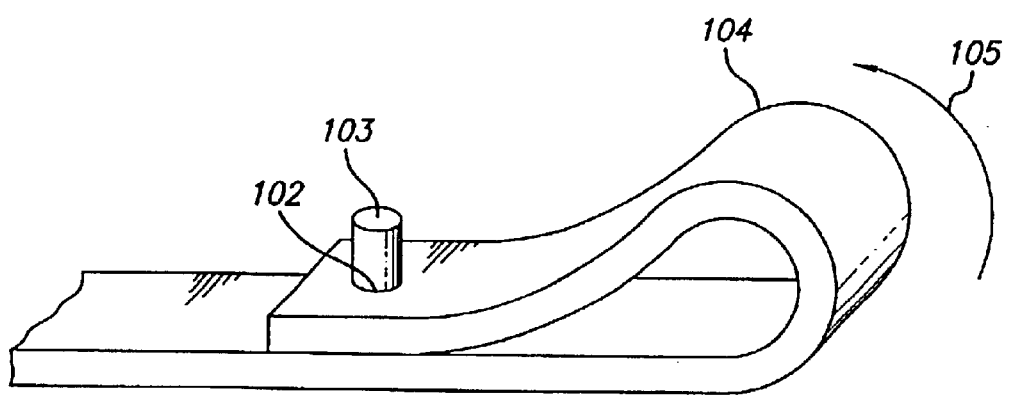
FIG. 14 is an elevational view of a portion of a link depicting an alternative attachment method to attach one cylindrical ring to an adjacent cylindrical ring.
Figure 15:
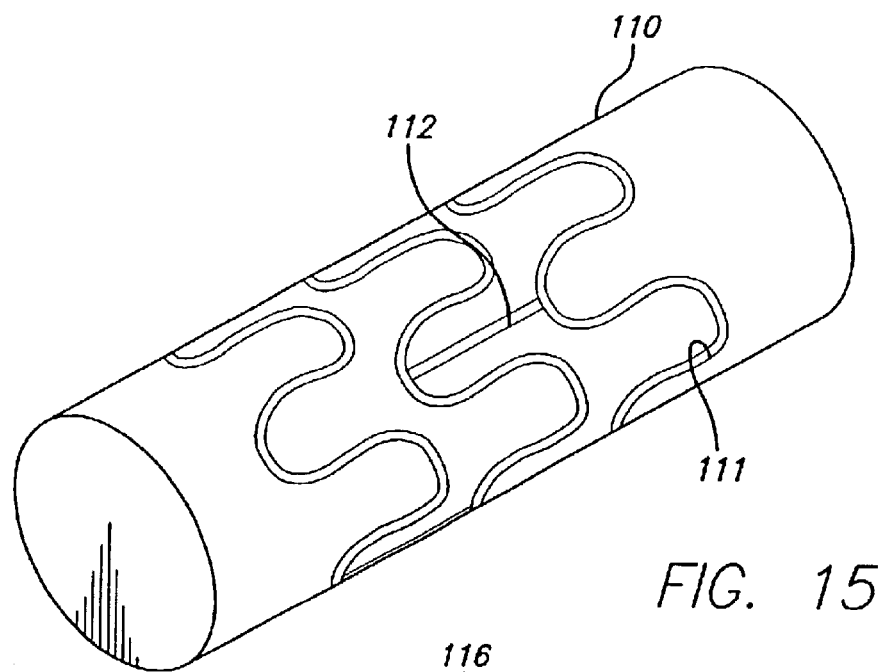
FIG. 15 is a perspective view of a mandrel having grooves for both the cylindrical rings and the links for use in the injection molding process.

In another embodiment illustrating the attachment of the link to the cylindrical ring, as shown in FIGS. 13 and 14, the link is heat-staked and wrapped around a portion of the cylindrical ring. More specifically, link 100 has a first end and an aperture 102 adjacent to first end. A stake 103 (or peg) is formed of a similar polymer material to that used for the links. The stake is positioned a short distance from the first end and is sized to create an interference with the aperture. In order to attach the link to a portion of the cylindrical ring, the first end of the link is wrapped around a portion of the cylindrical ring (not shown) in the direction of arrow 105 in order to form a loop 104. The stake is pushed through the aperture and should have a tight interference fit to form a locking relationship, or can be heated to flow the aperture and stake to form a more secure attachment.

As previously described, the links of the various embodiments of the invention are formed from a polymer material then attached in the manner described. With respect to the embodiments depicted in FIGS. 7–11, the links can be injection molded to fill the various cavities described to form the locking heads.

Figure 16:
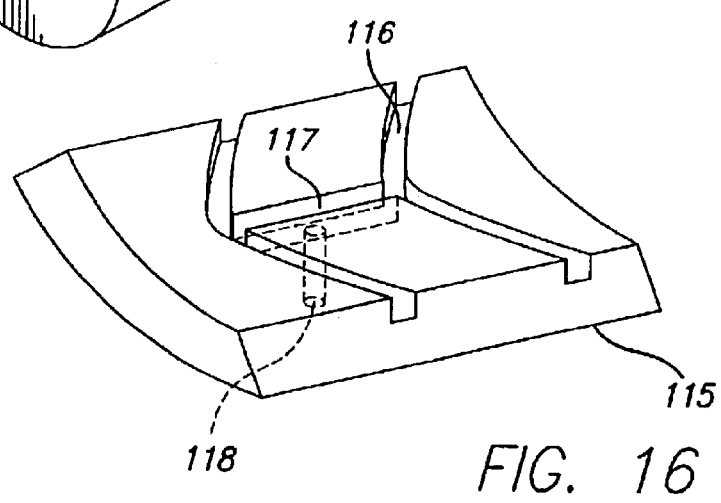
FIG. 16 is a perspective view of a quarter arc section of an outer mold cover having grooves for the cylindrical rings and links.
Figure 17:
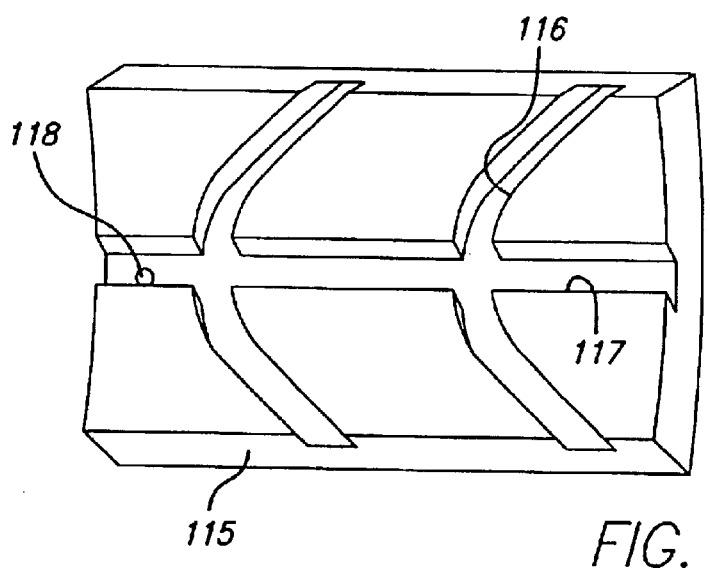
FIG. 17 is a perspective view of a quarter arc section of the outer mold cover having grooves for the cylindrical rings and links.
Figure 18:
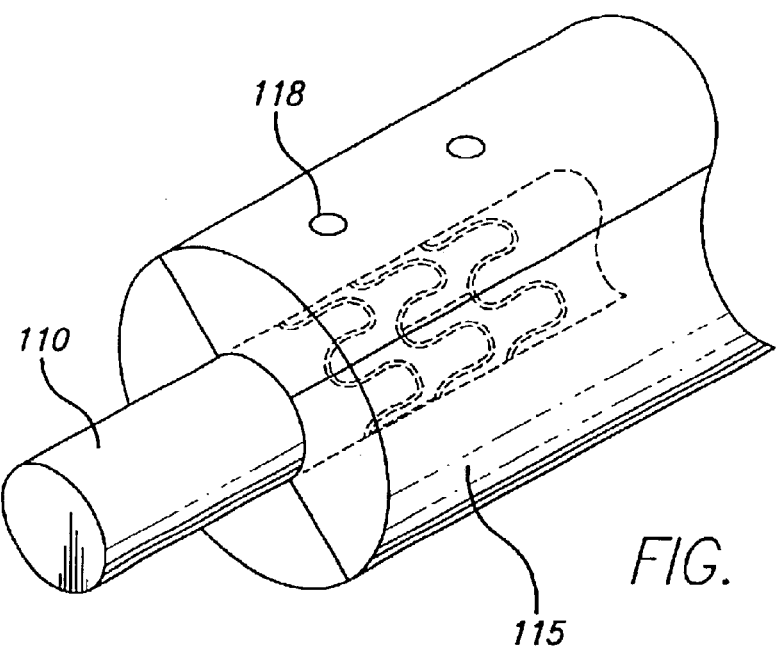
FIG. 18 is a partial perspective view of the mandrel with the quarter arc section outer mold covers positioned over the mandrel for use in the injection molding process.
Figure 19:
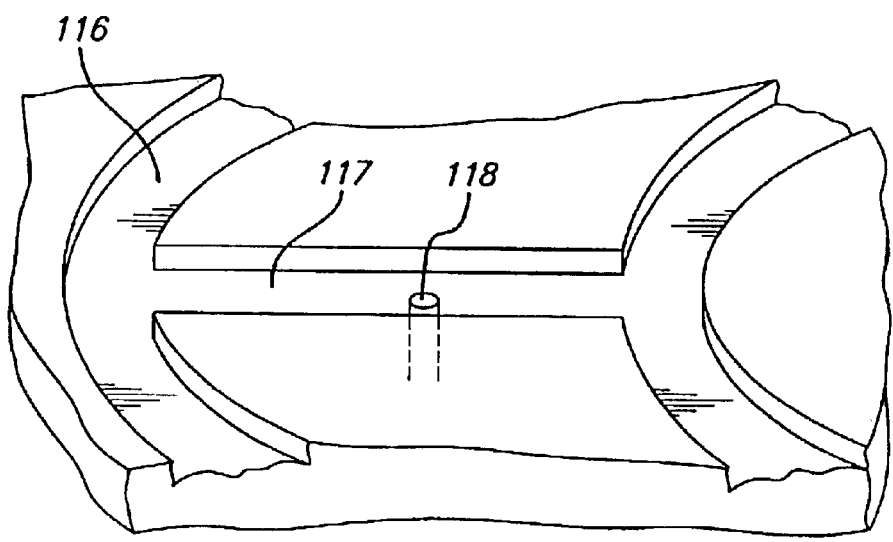
FIG. 19 is a partial elevational view of a portion of an outer mold cover depicting the gate through which the polymer is injected to form the links.

In keeping with one method of the invention for forming the links and attaching them to the cylindrical rings, an injection molding apparatus is shown in FIGS. 15–19. In keeping with the invention, a mandrel 110 is provided with grooves that correspond to the pattern of the cylindrical rings 12. The cylindrical rings are placed over the mandrel and fitted into the ring grooves 111. The mandrel also has link grooves 112 in which the injected polymer will flow in order to attach one cylindrical ring to an adjacent cylindrical ring. After the cylindrical rings are fitted into the ring grooves 111, and as shown in FIG. 16, a plurality of outer mold covers 115 are fitted around the mandrel and locked in place by known means, such as by clamping. The outer mold covers 115 typically are in cylindrical sections as depicted in FIGS. 16–19 and it is preferred that from two to four arc sections of outer mold covers be used to encase the mandrel 110. Each of the outer mold covers has grooves that correspond to grooves in the mandrel. Specifically, the outer mold covers have ring grooves 116 and link grooves 117 that correspond to the ring grooves 111 and link grooves 112 of the mandrel 110. The polymer used to form the links is injected by known techniques through gates 118 located at multiple positions along the outer mold covers. The gates provide openings or apertures through the outer mold coves to correspond to the location of the link grooves 112,117 so that as the polymer is injected through the outer mold cover, it will flow into the link groove 112,117 and form the link pattern.

After the outer mold covers and mandrel have a chance to cool so that the polymer solidifies, the outer mold covers 115 can be removed from the mandrel 110 and any excess flashing from the gates 118 can be removed by known means. The cylindrical rings 12 are then removed from the mandrel along with the links so that a completed stent with the rings attached to each other are formed.

Figure 20:
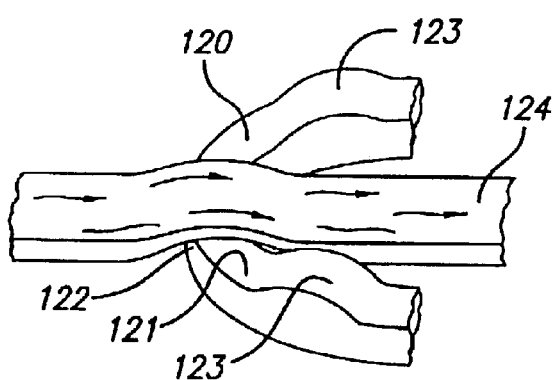
FIG. 20 is a partial elevational view of a section of a cylindrical ring having a thin and thick portion and a polymer link encapsulating the apex portion of the ring.

In an alternative embodiment, as shown in FIG. 20, the same mandrel 110 and outer mold covers 115 can be used to form polymer links to attach cylindrical rings that add varying degrees of thickness along portions of the cylindrical ring. For example, as shown in FIG. 20, a U-shaped portion 120 has a thinner portion 121 at the apex 122 and thicker portion 123 as you move away from the apex. In this configuration, once the cylindrical ring is mounted onto the mandrel, the outer mold covers 115 will require ring grooves 116 that correspond to the thinner and thicker portions 121,123 of the rings. Thereafter, the polymer injection process previously described to form the links is used to form link 124 which flows over the thinner portion 121 to connect one cylindrical ring to an adjacent cylindrical ring. In this embodiment, the polymer link 124 will encompass or flow around the U-shaped portion 120 at the apex 122 to form the attachment of the link to the cylindrical ring. Again, after the assembly has cooled and the polymer has solidified, the outer mold covers are removed and the stent is removed from the mandrel. Any excess polymer or flash can be removed by known methods.

With respect to the foregoing description of the polymer injection process, it is desirable that the cylindrical rings be placed on the mandrel 110 while the rings are in a somewhat expanded configuration. It is possible, however, to perform the injection mold process when the rings are in an unexpanded configuration on the mandrel, but it is easier in the expanded condition.

The link-to-ring attachment as shown in FIG. 12 can be accomplished by the mold injection process as described, only an adhesive is added at the end of the molding process to complete the attachment. For example, referring to FIG. 12 and FIGS. 16–19, the stent rings 12 are placed on the mandrel 110 as previously described to fit in ring grooves 111. The outer mold covers 115 are placed over the mandrel so that the mold cover ring grooves 116 correspond to the ring grooves 111, and the link grooves 117 correspond to the link grooves 112. After the polymer material is injected through gate 118, the assembly is allowed to cool and the outer mold covers are removed. Thereafter, the adhesive 97 can be added to fill first cavity 95 in the link and second cavity in the W-shaped portion 32. After the adhesive solidifies, the assembly is removed from the mandrel and the stent is formed by the link being attached to the cylindrical rings.

Similarly, for the link embodiments shown in FIGS. 9 and 10, the injection molding process is the same as that described for FIGS. 7, 8, and 11. Alternatively, the links 60 and 70 can be heat staked onto the locking head 62 and first locking head 73 and second locking head 74 respectively. For example, the area around the locking heads can be heated so that as the link 60,70 is pushed onto the locking heads, the polymer material softens and the locking head penetrates the polymer material until the link tip 65 and 77 abuts the W-shaped portion 32 and Y-shaped portion 33 respectively. After the polymer cools, the teeth 63 and 75 assist in attaching the link to the cylindrical ring.

With respect to all of the aforedescribed embodiments in which polymer links are used to connect adjacent rings, one or more metal links may be required between adjacent rings to provide better relative orientation between the rings. Also, the metal links will provide more structural support during delivery and after the stent has been expanded and implanted in the artery or other vessel. Thus, it is in keeping with the invention that both polymer links and metal links may be used in any of the stent embodiments disclosed without departing from the invention.

One method of making the stent 10 of the invention is to first laser cut the cylindrical rings 12 from a tube so that the rings are not connected by the aforedescribed polymer links 13. The rings are then placed on a mandrel into stent-patterned grooves and encased with a locking sleeve having a mirror of the stent pattern cut into its inner surface. The only exposed region of the stent is the channels that correspond to the links that will connect the rings. The mandrel and the encapsulating sleeve permit the injection of a polymer which fills the channels corresponding to the links. The polymer is used to form the links which connect adjacent rings. The stent forming processes are described in more detail with the description of the formation of the stent cylindrical rings 12 by a laser cutting process.

The afordescribed illustrative stent 10 and similar stent structures can be made in many ways. One method of making the stent rings 12 is to cut a thin-walled tubular member, such as stainless steel tubing to remove portions of the tubing in the desired pattern for the stent, leaving relatively untouched the portions of the metallic tubing which are to form the rings. In accordance with the invention, it is preferred to cut the tubing in the desired pattern using a machine-controlled laser as illustrated schematically in FIG. 6.

The tubing may be made of suitable biocompatible material such as stainless steel, cobalt-chrome (CoCn, NP35N), titanium, tantalum, nickel-titanium (NiTi), and similar alloys. The stainless steel tube may be Alloy type: 316LSS, Special Chemistry per ASTM F138-92 or ASTM F139-92 grade 2. Special Chemistry of type 316: per ASTM F 138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

The tubing is put in a rotatable collet fixture of a machine-controlled apparatus for positioning the tubing relative to a laser. According to machine-encoded instructions, the tubing is rotated and moved longitudinally relative to the laser which is also machine-controlled. The laser selectively removes the material from the tubing by ablation and a pattern is cut into the tube. The tube is therefore cut into the discrete pattern of the finished cylindrical rings.

Cutting a fine structure (0.0035 inch web width) requires minimal heat input and the ability to manipulate the tube with precision. It is also necessary to support the tube yet not allow the stent structure to distort during the cutting operation. In one embodiment, the tubes are made of stainless steel with an outside diameter of 0.060 inch to 0.095 inch and a wall thickness of 0.002 inch to 0.004 inch. These tubes are fixtured under a laser and positioned utilizing a CNC to generate a very intricate and precise pattern. Due to the thin wall and the small geometry of the stent pattern (0.0035 inch typical strut or ring width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd/YAG, typically available from Quantronix of Hauppauge, N.Y., that is frequency doubled to produce a green beam at 532 nanometers is utilized. Q-switching produces very short pulses (<100 nS) of high peak powers (kilowatts), low energy per pulse ($\leq 3$ mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle (0.018 inch I.D.) is centered around the focused beam with approximately 0.010 inch between the tip of the nozzle and the tubing. The jet is pressurized with oxygen at 20 psi and is directed at the tube with the focused laser beam exiting the tip of the nozzle (0.018 inch dia.) The oxygen reacts with the metal to assist in the cutting process very similar to oxy-acetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034 inch dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005 inch) with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCL for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stent rings are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110–135° F. and the current density is about 0.4 to about 1.5 amps per in.$^2$. Cathode to anode area should be at least about two to one.

Direct laser cutting produces edges which are essentially perpendicular to the axis of the laser cutting beam, in contrast with chemical etching and the like which produce pattern edges which are angled. Hence, the laser cutting process essentially provides strut cross-sections, from cut-to-cut, which are square or rectangular, rather than trapezoidal.

The foregoing laser cutting process to form the cylindrical rings 12 can be used with other metals including cobalt-chrome, titanium, tantalum, nickel-titanium, and other bio-compatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

Generally speaking, links 13 can be formed by injection molding by the methods described herein. Some examples of materials that can be used to form the links include polyurethanes, polyetherurethanes, polyesterurethanes, silicone, thermoplastic elastomer (C-flex), polyether-amide thermoplastic elastomer (Pebax), fluoroelastomers, fluoro-silicone elastomer, styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidents, polymers augmented with image enhancing materials (e.g., barium sulfate), polymers having a proton (H+) core, polymers augmented with protons (H+), butadiene and isoprene (Kraton) and polyester thermoplastic elastomer (Hytrel).

While the invention has been described in connection with certain disclosed embodiments, it is not intended to limit the scope of the invention to the particular forms set forth, but, on the contrary it is intended to cover all such alternatives, modifications, and equivalents as may be included in the spirit and scope of the invention as defined by the appended claims.

What is claimed:

1. An intravascular stent, comprising:

a plurality of flexible cylindrical rings being expandable in a radial direction, each of the rings having a first delivery diameter and a second implanted diameter and being aligned on a common longitudinal axis;

each of the rings being formed of a first material;

a plurality of flexible links, each of the links having sufficient column strength to axially separate the cylindrical rings;

wherein the first material is a metallic material;

at least one of the links being formed of a second material more flexible than the first material;

wherein the second material is a polymeric material:

each of the links having a first end and a second end, the first and second ends being coupled to adjacent cylindrical rings to couple adjacent cylindrical rings together; and at least one link being coupled between each pair of adjacent cylindrical rings.

2. A process for providing an intravascular stent, comprising:

providing a plurality of flexible cylindrical rings being expandable in a radial direction, each of the rings having a first delivery diameter and a second implanted diameter;

the flexible cylindrical rings being aligned on a common longitudinal axis;

at least one of the flexible cylindrical rings being formed of a metallic material;

providing a plurality of flexible links, each of the links having a first end and a second end, the first and second ends being coupled to adjacent flexible cylindrical rings to couple adjacent flexible cylindrical rings together and each of the links having sufficient column strength to axially separate the flexible cylindrical rings;

at least one of the links being formed of a polymeric material that is more flexible than the metallic material; and at least one link being coupled between each pair of adjacent flexible cylindrical rings.

* * * * *